Figure 1:
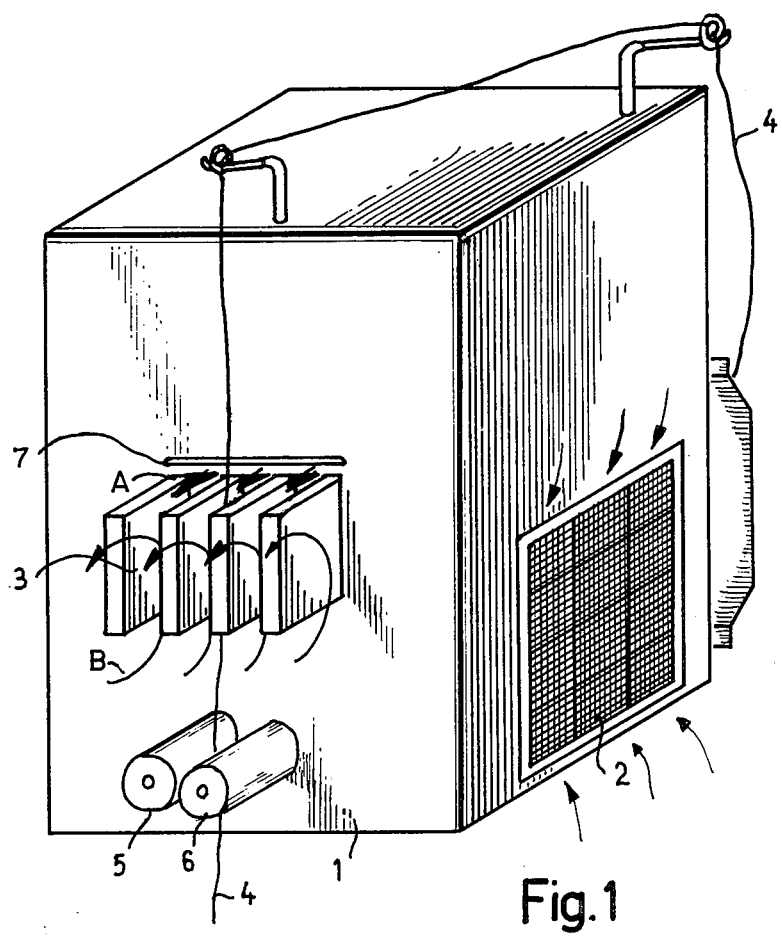

United States Patent [19]

Heusser

[11] 3,960,593

[45] June 1, 1976

[54] METHOD OF INCREASING THE LONG-TERM STABILITY OF A MEASURING ELEMENT OF TEXTILE TESTERS

[75] Inventor: Eduard Heusser, Uster, Switzerland

[73] Assignee: Zellweger, Ltd., Switzerland

[22] Filed: Sept. 23, 1974

[21] Appl. No.: 508,624

[30] Foreign Application Priority Data
Sept. 26, 1973  Switzerland.................... 13805/73

[52] U.S. Cl................................. 134/37; 134/36; 34/13; 34/20; 73/160
[51] Int. Cl.²........................................ B08B 5/00
[58] Field of Search............. 134/37, 36; 34/13, 20; 73/160

[56] References Cited
UNITED STATES PATENTS
2,175,608   10/1939   Lawrence et al..................... 134/37
3,440,097   4/1969   Gleaton.............................. 134/37

*Primary Examiner*—Arthur D. Kellogg
*Attorney, Agent, or Firm*—Craig & Antonelli

[57] ABSTRACT

A method of increasing the long-term stability of a measuring element for a textile testing apparatus, said measuring element including a plurality of parallel plate-like components which comprises causing an artificial airstream to sweep over the top of the measuring element to form a secondary air convection which maintains constant ambient conditions in the vicinity of the measuring element.

5 Claims, 2 Drawing Figures

U.S. Patent June 1, 1976 3,960,593

METHOD OF INCREASING THE LONG-TERM STABILITY OF A MEASURING ELEMENT OF TEXTILE TESTERS

This invention relates generally to a textile testing apparatus for measuring the cross-section of yarns, rovings, slivers and the like and in particular to a method of and a device for increasing the long-term stability of a measuring element of such textile testing apparatus.

Various kinds of testing apparatus are known in the textile industry which comprise a measuring element projecting from the housing of the apparatus in which certain properties of the material to be tested are made measurable by conversion into a proportional electrical signal in the measuring element. Several of these apparatus employ measuring elements in the form of a capacitor having a plurality of electrodes. Such apparatus is disclosed in U.S. Pat. Nos. 3,754,172; 3,788,138 and 3,805,607, the disclosures of which are incorporated herein by reference.

Measuring elements of the kind in question are extremely sensitive to changes in the atmosphere surrounding them, such as its temperature, its humidity level and any uncontrolled airflows, and to mechanical changes in their immediate surroundings attributable, for example, to the deformation of components of the measuring element due to unstable temperature conditions between the interior and exterior of the testing apparatus and to the deposition of foreign matter on the measuring element itself. Textile machinery in particular is prone to very heavy soiling, because textile materials give off large quantities of dust during processing. Accumulations of fibers can be found at every processing station, and are carried away by even gentle airflows only to be deposited again somewhere else. Although the adverse effects of fiber accumulations can be eliminated by suitable measures, and although attempts have been made to avoid marked differences in the immediate surroundings, influences of this kind cannot be completely kept away from the extremely sensitive measuring elements.

It has also been proposed to expose the measuring element to an airstream in order, on the one hand, to prevent the deposition of fibers and, on the other hand, to neutralize the effect of the heat produced in the textile testing apparatus and dissipated outwards through the measuring elements. Unfortunately, attempts in this direction have not been altogether successful insofar as, although deposits of fiber dust have been eliminated, expectations of a measuring element with long-term stability have not been fulfilled. Although this failure cannot be entirely explained by plausible arguments, practical experience has shown this measure to be inappropriate.

The present invention is based on such experience and produces a method of increasing the long-term stability of the measuring element of textile testing apparatus in which a secondary airstream which maintains uniform ambient conditions around the measuring element is formed in the vicinity of the measuring element, from an artificial airstream sweeping over the top of the measuring element.

The invention also provides a device for carrying out this method, which comprises an air-outlet opening above the measuring element from which air is blown out over the measuring element, maintaining a convection effect in the surrounding air between the components of the measuring element.

Whereas, on the one hand, direct exposure of the measuring element to air issuing from an opening has an adverse effect upon the measuring element, and whereas on the other hand, the total prevention of airflow in the vicinity of the measuring element does not result in any increased instability either, it has been found that an intermediate solution, in which a weak eddy current feeding exclusively off the ambient air is formed in the vicinity of the measuring element, produces a distinct improvement in long-term stability.

In this way, an airstream issuing from the housing of the testing apparatus, which could be uncontrollably heated through electrical components inside the apparatus and whose relative humidity in this form is indeterminate, is prevented from directly influencing the measuring element. By contrast, the secondary, induced airstream has the same temperature and moisture level as the atmosphere surrounding the textile testing apparatus which can be regarded as sufficiently constant, even in the long term.

Figure 2:
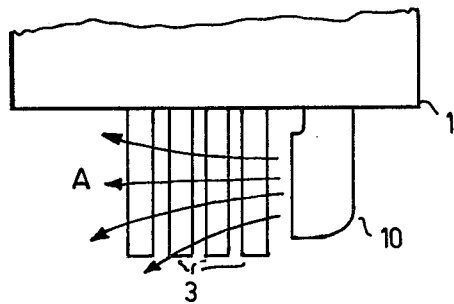

Some embodiments of the invention will now be described by way of example with reference to the accompanying drawings, in which:

FIG. 1 illustrates a first embodiment of the device;
FIG. 2 shows another possible embodiment.

The device illustrated in FIG. 1 comprises a housing 1 which accommodates a fan which sucks in the surrounding air through an air filter 2 and delivers it into the housing. This results in the formation inside the housing of an excess pressure which attempts to escape through any gaps present and through other openings intentionally provided in the wall of the housing. A measuring element 3, for example, a measuring capacitor of the type described in U.S. Pat. No. 3,754,172 is arranged outside the housing and a textile material 4, e.g. a yarn to be tested, is drawn through the element 3 by delivery rollers 5, 6 in a known manner.

The wall of the housing above the measuring capacitor is provided with horizontally arranged slot 7 through which the excess pressure prevailing inside the housing 1 flows out substantially horizontally in the direction of the arrows A and blows away any fiber dust which attempts to settle on the top of each of the plurality of test electrodes forming one measuring capacitor. As shown, the test electrodes are arranged substantially parallel to each other with adjacent electrodes defining vertical slots through which the yarn to be tested is drawn. Naturally, the airstream should not be so intense that the material 4 being tested is blown out of the range of the test electrodes.

The airstream sweeping over the top of the test electrodes forms an eddy current in the slots formed by the test electrodes by virtue of the fact that air is carried upwards from below the measuring element between the test electrodes in the direction of the arrows B and kept in constant motion.

It is not only the primary airstream A, but also the secondary air circulation B, which prevents fiber dust from settling in the vicinity of the measuring element 3. In addition, the circulation of air around the test electrodes (convection B) has a cooling effect and stabilizes the surface temperature of the measuring element 3.

Another effect of the permanent circulation of fresh air inside the housing of the testing apparatus is that the components, e.g. the electrodes, which heat up during operation are permanently cooled, which is another advantage so far as the stability of the measuring element is concerned. Naturally, the air filter 2 has to be periodically cleaned or replaced, although this can readily be done by suitably designing the mountings for the air filter.

A similar effect of the airstream is also obtained if, instead, of the airstream issuing from the housing in the direction of the test electrodes as illustrated in FIG. 1, it is directed through suitable guide ducts 10 laterally along the front of the housing over the upper edges of the parallel test electrodes, as illustrated in FIG. 2.

In this case, a secondary air convection B is also directed from the space below the measuring element through its components, i.e. its electrodes, onto the upper side, producing the already mentioned favorable effects upon the stability of the measuring element.

The device according to the invention is not confined in its application to capacitive measuring elements, but instead can also be effectively used for example in optical or acoustic measuring systems which have at least two components, especially plate-like components, arranged outside of a housing and spaced from each other to define a passage or passages therebetween.

While the novel embodiments of the invention have been described, it will be understood that various omissions, modifications and changes in these embodiments may be made by one skilled in the art without departing from the spirit and scope of the invention.

What is claimed is:

1. A method of increasing the long-term stability of a measuring element for a textile testing apparatus, said measuring element having a plurality of parallel plate-like components arranged outside of a housing which form at least one passage between adjacent components, which comprises forming a secondary air convection which maintains constant ambient conditions in the vicinity of the measuring element by causing an artificial airstream to sweep over the top of the measuring element, said airstream promoting said secondary air convection in the form of eddy currents within said passage.

2. The method of claim 1, wherein the airstream is directed longitudinally over the measuring element.

3. The method of claim 1, wherein the airstream is directed transversely over the measuring element.

4. The method of claim 1, wherein said artificial airstream is caused to sweep over said plurality of parallel plate-like components in a direction parallel to said plate-like components.

5. The method of claim 1, wherein said artificial airstream is caused to sweep over said plurality of parallel plate-like components in a direction transverse to said plate-like components.

* * * * *